United States Patent [19]

Gollobin

[11] Patent Number: 5,334,195
[45] Date of Patent: Aug. 2, 1994

[54] METHOD AND ARTICLE FOR REMOVING SPLINTERS WITH A DISPOSABLE LANCET

[76] Inventor: Peter Gollobin, 9 Meadow La., Glen Head, N.Y. 11545

[21] Appl. No.: 651,148

[22] Filed: Feb. 6, 1991

[51] Int. Cl.$^5$ ............................................. A45D 26/00
[52] U.S. Cl. ................................... 606/131; 606/181
[58] Field of Search ............... 606/131, 133, 167, 181, 606/182, 183, 184, 185

[56] References Cited

U.S. PATENT DOCUMENTS

| | | | |
|---|---|---|---|
| D. 189,077 | 10/1960 | Gollobin | 606/181 |
| 3,046,987 | 7/1962 | Ehrlich | 606/181 |
| 4,790,316 | 12/1988 | Bogdan | 606/133 |

FOREIGN PATENT DOCUMENTS 464916  3/1952  Italy ..................... 606/181

*Primary Examiner*—C. Fred Rosenbaum
*Assistant Examiner*—Manuel Mendez
*Attorney, Agent, or Firm*—Galgano & Burke

[57] ABSTRACT

A method and article for removing splinters where a disposable lancet is used to pierce the patient's skin in an area surrounding or adjacent to the splinter and remove the splinter. The method also provides for loosening the skin in the area adjacent to the splinter before removal by tearing the skin with the sharp point of the lancet.

2 Claims, 1 Drawing Sheet

METHOD AND ARTICLE FOR REMOVING SPLINTERS WITH A DISPOSABLE LANCET

BACKGROUND OF THE INVENTION

The invention relates to an improved method and article for removing foreign objects commonly called "splinters". More particularly, the invention relates to such a method utilizing a pre-sterilized, individually wrapped, disposable lancet having a flat point.

The method for removing splinters according to prior art is well known. It is very common for a person who wishes to remove a splinter or other small foreign objects from the skin of themselves, other persons, or an animal to use a needle or pin which they attempt to sterilize by heating or wiping with alcohol.

There are two basic problems in this method of removing foreign objects. First, sterilizing by heating a needle or pin using a stove or match is not an adequate method of sterilization. It often puts carbon deposits on the needle and wiping with alcohol does not sterilize against hepatitis spores and other infectious agents. Second, a needle or pin is conical in shape, tapering to a point and usually polished, which is good for piercing, but not very good for pulling out foreign objects or for loosening the skin around a foreign object so that it can be removed.

SUMMARY OF THE INVENTION

It is therefore an object of the present invention to provide a method where a splinter or foreign object may be easily removed with a pre-sterilized instrument.

It is a further object that such method provide an individually wrapped, disposable sterilized lancet which is easily manufactured and relatively inexpensive.

These and other related objects are achieved according to the invention by a method for removing a splinter from a patient's skin. The method includes the steps of piercing the patient's skin in an area adjacent to the splinter (i.e., underneath or above the splinter or foreign matter) with a hand-held, disposable, elongated lancet. The lancet has a handle portion at one end and a flat point at its other end. The splinter is then removed from the patient's skin by effective manipulation of the flat point of the lancet relative to the splinter. Most advantageously, the lancet is removed from an individually wrapped pre-sterilized package prior to the step of piercing the skin.

Preferably, the lancet is a metal lancet, made from corrosion resistant stainless steel, and its flat point has one or two sharpened edges. In a preferred embodiment, the flat point of the lancet has a length in the range of 2/64" to 5/16" and the lancet has an overall length in the range of 0.375" to 2.50". The overall width is in the range of ⅛" to ⅜". The lancet is most desirably provided with a set of raised knurls along the handle portion to aid in manipulating the device. The thickness of the lancet, excluding the raised knurls, is ideally in the range of 0.003" to 0.015".

In a particularly preferred embodiment, the method includes the step of tearing the patient's skin in an area adjacent to (i.e., above or underneath) the splinter. Such a tearing is achieved by piercing the skin with the point of the lancet adjacent to or above or below the splinter and then pulling the point away from the skin in a direction perpendicular to the entry direction. Because of the flat shape of the point, either the skin tears easily to loosen the splinter or it lifts the splinter out directly.

Other objects and features of the present invention will become apparent from the following detailed description, considered in connection with the accompanying drawings which disclose the embodiments of the invention. It is to be understood, however, that the drawings are designed for the purpose of illustration only, and not as a definition of the limits of the invention.

BRIEF DESCRIPTION OF THE DRAWINGS

In the drawings, wherein similar reference characters denote similar elements throughout the several views.

DETAILED DESCRIPTION OF THE PREFERRED EMBODIMENT

Figure 1:
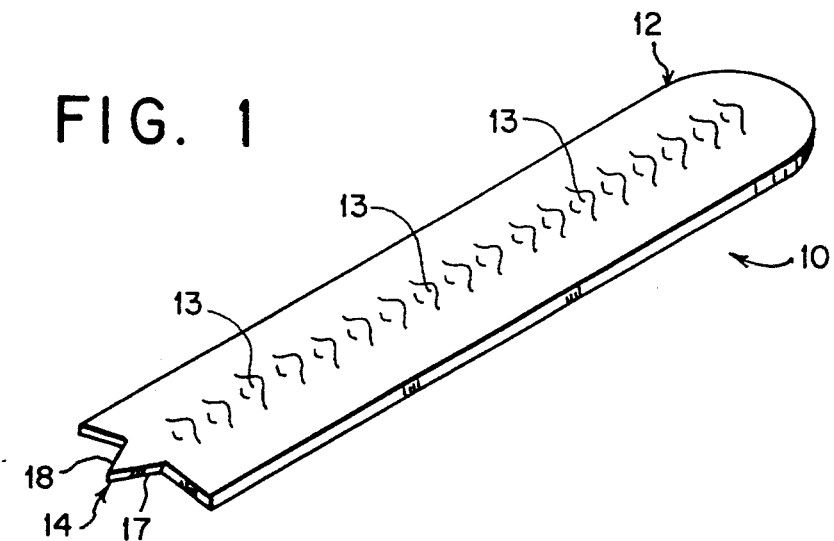
FIG. 1 is a perspective view of the disposable lancet used in the present method.
Figure 2:
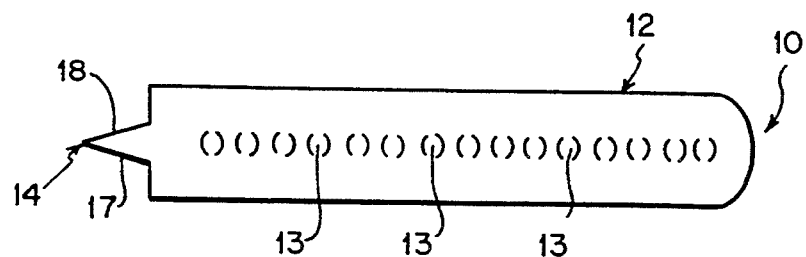
FIG. 2 is a top elevational view thereof.
Figure 4:
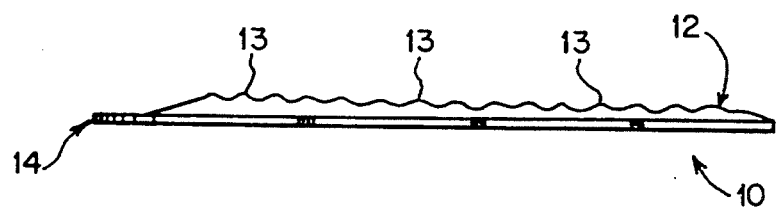
FIG. 4 is a bottom side elevational view.

Referring now in detail to the drawings and, in particular to FIGS. 1-4, there is illustrated a disposable lancet 10, according to the present invention. This type of lancet is preferred for use in the method embodying the present invention, for removing foreign objects from skin. The lancet is made from, for example, corrosion resistant stainless steel. There are many types of lancets which can be employed in connection with the invention. The lancet has a handle area 12 with raised embossed knurls 13 and a point 14. The shape of the point is made up of intersecting flat planes from either a stamping process or grinding process.

Up until now, this type of lancet was used to puncture skin in order to draw blood for blood tests. A presterilized lancet would be removed from its individual packet and used to prick the finger of the person whose blood needs testing. The lancet would then be discarded.

It was surprisingly found that although this type of lancet has been used for years to draw blood, it has never been marketed or even recognized for splinter or other foreign object removal, while its flat surface and blade or opposing blades are ideal for this purpose. The disposable lancet 10 ideally is packaged in an individual pre-sterilized packet. The packets could be sold, for example, in a small container with ten or twenty disposable lancets. The lancet is removed from the packet and held by handle area 12 which may be provided with raised embossed knurls 13 of any desired design which will aid in gripping and also add to the rigidity of the lancet.

An effective lancet according to the invention will have the following general dimensions: the flat point can range in length from 2/64" to 5/16"; the overall length can range from 0.375" to 2.50"; the width can range from ⅛" to ⅜"; and the thickness of the lancet, excluding any raised gripping portions, can range from 0.003" to 0.015".

The following dimensions are set forth as the preferred dimensions for one type of lancet (as shown in the drawings), but they are not intended to limit the invention. The lancet ideally has a length of 1 21/32"±1/32", inclusive of the point. The width is approximately 15/64" and the height 0.007" non-inclusive of the raised knurls. The total height including the raised knurls would be in the range of 0.025"-0.032".

A single row of knurls lies in the center of the handle area and is approximately 0.07" wide and extends 1 5/16" along the length. Each knurl has an area of 1/16" by 1/16".

The length of the point is 7/64"±1/64". The point, as stated above, is in the shape of intersecting flat planes. The planes should be offset with regard to each other 25°±3°. In the event that a long point is desired, its point length would be 5/32"±1/64".

Figure 5:
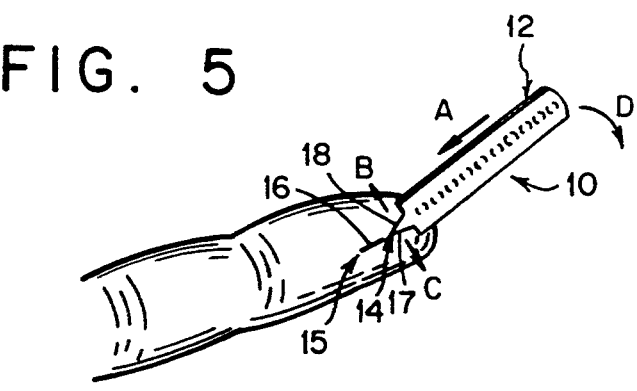
FIG. 5 is a perspective view of the blood lancet in use.
Figure 3:
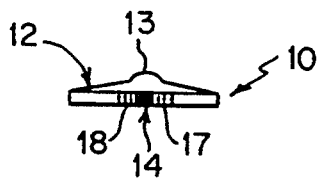
FIG. 3 is a left side elevational view.

Returning now to a description of the method, the sterilized lancet would be removed from its package and the user, grasping the handle area 12 of lancet 10 in a somewhat pen-like grip, would manipulate the lancet so that the point 14 is brought toward the skin area 15 containing the foreign object, as shown in FIG. 5, in the direction of arrow A. The user then applies sufficient pressure on the handle (in the direction of arrow A) such that point 14 then pierces the skin just under the foreign object 16. Since point 14 is a flat surface, when the point is manipulated in an upward direction away from the skin (shown by the direction of arrow D) it can actually pull out the foreign object. A conical needle or pin cannot easily pull an object out because it has a round polished and tapering surface area and the object will tend to slide off the point.

Lancet 10 can also be used to loosen the skin around the splinter or foreign object. By piercing the skin adjacent to the foreign object and then lifting the lancet 10 in a direction perpendicular to the entry direction, the flat blades 17 and 18 can easily tear the patient's skin in directions B and C in FIG. 5. This can open the area adjacent to the foreign object or directly above it and thereby loosen it. Such a tearing action, by a needle or pin perpendicular to the direction of entrance of the needle or pin is not as effective due to its shape. Skin and foreign objects will tend to easily slide off the tapering polished conical point of a needle or pin instead of tearing the skin, as with a flat point.

Once the skin surrounding the foreign object has been loosened up, lancet 10 can be utilized to lift or scoop the foreign object out by lifting away from the skin.

In this regard, the lancet can also be manipulated to pierce the skin, adjacent and parallel to the splinter, in the direction of arrow A. The rear end of handle area 12 can then be pivoted downwardly away from the splinter (as shown by direction D), causing point 14 to move into or under the splinter. Removal of the lancet at this point makes it highly likely that the splinter can be dislodged.

Thus, while only one embodiment of the present invention has been shown and described, it is to be understood that many changes and modifications may be made thereunto without departing from the spirit and scope of the invention as defined in the appended claims.

What is claimed is:

1. A method for removing a splinter from a patient's skin comprising:

removing the lancet from an individually wrapped pre-sterilized package, piercing the patient's skin in an area adjacent to said splinter with a hand-held, disposable, elongated metal, generally flat lancet, having a handle portion at one end and a flat V-shaped point at its other end said flat point of said lancet having a length in the range of 2/64" to 5/16", said lancet having an overall length in the range of 0.375" to 2.50", said lancet having an overall width in the range of ⅛" to ⅜', and said lancet having a thickness in the range of 0.003" to 0.015", tearing the patient's skin by piercing the skin adjacent to the splinter and then lifting the lancet in a direction perpendicular to the entry point in the patient's skin in a repetitive fashion so as to loosen the skin around the splinter, and thereafter placing said flat point of said lancet under said splinter and lifting it away from the skin so as to dislodge said splinter.

2. The method as claimed in claim 1, wherein said lancet has a set of raised knurls along said handle portion to aid in manipulating the device.

* * * * *